United States Patent
Duflot et al.

(10) Patent No.: US 8,112,935 B2
(45) Date of Patent: Feb. 14, 2012

(54) METHOD FOR PRODUCING A POWDER CONTAINING XYLITOL CRYSTAL PARTICLES WITH ANOTHER POLYOL

(75) Inventors: Pierrick Duflot, La Couture (FR); Baptiste Boit, Bethune (FR)

(73) Assignee: Roquette Freres, Lestrem (FR)

( * ) Notice: Subject to any disclaimer, the term of this patent is extended or adjusted under 35 U.S.C. 154(b) by 947 days.

(21) Appl. No.: 11/995,036

(22) PCT Filed: Jun. 28, 2006

(86) PCT No.: PCT/FR2006/001507
§ 371 (c)(1),
(2), (4) Date: May 12, 2008

(87) PCT Pub. No.: WO2007/006885
PCT Pub. Date: Jan. 18, 2007

(65) Prior Publication Data
US 2009/0007903 A1 Jan. 8, 2009

(30) Foreign Application Priority Data
Jul. 8, 2005 (FR) ...................................... 05 07327

(51) Int. Cl.
*A01C 1/00* (2006.01)
(52) U.S. Cl. ................................. 47/58.1 SE; 47/DIG. 9
(58) Field of Classification Search ............... 47/58.1 R, 47/58.1 SE, FOR. 100, DIG. 9, 66.6, 86, 47/57.6; 127/29, 60; 504/100
See application file for complete search history.

(56) References Cited

U.S. PATENT DOCUMENTS

| | | | |
|---|---|---|---|
| 5,679,398 A | 10/1997 | Serpelloni et al. | |
| 6,331,504 B1 * | 12/2001 | Balsevich | 504/100 |
| 2002/0110633 A1 * | 8/2002 | Beauregard et al. | 426/658 |
| 2003/0224936 A1 * | 12/2003 | Kretzschmar | 504/100 |
| 2008/0132411 A1 * | 6/2008 | Watt et al. | 504/100 |

FOREIGN PATENT DOCUMENTS

| | | |
|---|---|---|
| EP | 0 528 604 A1 | 2/1993 |
| EP | 0528604 | 2/1993 |
| EP | 1 072 578 A1 | 1/2001 |
| EP | 1072578 | 1/2001 |
| EP | 1 207 164 A2 | 5/2002 |
| EP | 1207164 | 5/2002 |
| FR | 2 202 867 A | 5/1974 |
| FR | 2202867 | 5/1974 |
| GB | 1481846 | 8/1977 |
| WO | 96/07331 A1 | 3/1996 |
| WO | 2004/005227 A1 | 1/2004 |
| WO | WO 2004/005227 | 1/2004 |
| WO | 2004/106273 A2 | 12/2004 |
| WO | WO 2004/106273 | 12/2004 |

OTHER PUBLICATIONS

International Search Report of PCT/FR2006/001507 filed Jun. 28, 2006, date of mailing Feb. 5, 2007.

* cited by examiner

*Primary Examiner* — T. Nguyen
(74) *Attorney, Agent, or Firm* — Young & Thompson

(57) ABSTRACT

A method for producing a powder containing xylitol crystal particles and another polyol including a mixture containing a xylitol syrup and another polyol, whose dry material content is equal to or greater than 95% by weight, xylitol content ranges from 85 to 97.5% by weight and the other polyol content ranges at least from 15 to 2.5% by weight with respects to the dry material. The method includes: obtaining the mixture by simultaneously dispersing the xylitol and the other polyol syrup and xylitol-containing germs in an open rotating vessel containing xylitol-based granules, mixing the xylitol and the other polyol syrup and xylitol-containing germs on the surface of the xylitol-containing germs contained in the vessel, removing the xylitol-based granules and the other polyol from the vessel and crystallizing the xylitol and other polyol contained in the granules.

14 Claims, No Drawings

METHOD FOR PRODUCING A POWDER CONTAINING XYLITOL CRYSTAL PARTICLES WITH ANOTHER POLYOL

The invention relates to a method for continuous manufacture of a powder containing crystalline particles of xylitol with another polyol in a lower proportion.

The expression "other polyol" is understood in the sense of the invention to mean a polyol preferably chosen from the group consisting of threitol, erythritol, arabitol, ribitol, sorbitol, mannitol, maltitol, maltotriitol, maltotetraitol, lactitol, hydrogenated isomaltulose, glycerol and hydrogenated starch hydrolysates, taken alone or in combination.

More preferably, this other polyol is chosen from the group consisting of sorbitol, maltitol, mannitol and hydrogenated isomaltulose, taken alone or in combination.

The expression "lower proportion" is understood in the sense of the invention to mean a content of this other polyol, in the powder containing crystalline particles of xylitol, between 2.5 and 15 wt %, preferably from 5 to 10 wt % of the total amount of polyols.

Xylitol is a polyol with 5 carbon atoms, resulting from the hydrogenation of xylose. It is used as a sugar substitute and/or as a support substance in pharmaceutical preparations and in the food industry, in particular in the form of tablets to be sucked or chewed.

It is already known how to manufacture crystallized xylitol, for example by inducing the crystallization of said xylitol in a syrup that is sufficiently rich in this product and is sufficiently purified. Thus, single-crystals of tetrahedral form, having a relatively uniform size, are obtained.

However, pure xylitol has very poor compressive properties, regardless of the type of manufacture implemented.

In order to improve these properties, it is known in the prior art to propose to manufacture xylitol powders having a xylitol content of more than 90 wt %, the remainder of the total polyol content being provided by another polyol, such as sorbitol.

It has been proposed in Patent EP 528 604 to carry out the co-crystallization of xylitol and of sorbitol, the ratio of sorbitol to xylitol being between 50/50 to 97/3, preferably between 65/35 and 95/5.

Besides the fact that these co-crystals incorporate more than 50% of sorbitol (xylitol is instead, in this case, the minority component of the mixture), the mixture does not in any case have exceptional compressive properties.

It is also proposed in Patent DE 19845339 to carry out the co-atomization of xylitol at more than 90 wt % with sorbitol, or by granulating said mixture in a fluidized bed.

The results show that pure xylitol granulated by spraying is not suitable for a direct conversion into tablets without other additives. At a pressure of 20 kN, the hardness of the tablets, of around 60 N, is too low and the abrasion is too high for the tablets manufactured.

For the experts in the field in question, the hardnesses can, in effect, only be achieved in practice when xylitol is granulated with carboxymethyl cellulose (CMC) in an amount, for example, of 2 wt %.

International Patent Application wO 92/10168 also describes a process for manufacturing directly compressible xylitol granules consisting of the wet granulation of finely milled xylitol by the use of a binder which may be a sodium carboxymethyl cellulose solution, a polydextrose solution or else a hydrogenated maltose syrup. A final drying step is obligatory. Thus granules containing 0.1 to 5% of binder are obtained.

However, the CMC contained in the tablets has disadvantageous repercussions on the organoleptic properties.

It has also been proposed, in Patent FR 2 336 123 to manufacture chewable tablets from a dry mix of xylitol in an amount of 10 to 80 wt % and of a polyol in an amount of 80 to 10 wt %, relative to the weight of the tablet. The polyol may be sorbitol, mannitol or a mixture of these.

It emerges from the description of this patent application that the polyol represents at least 50 wt % relative to the xylitol. The latter cannot therefore be considered as the main component of the powder to be compressed. Under these conditions, it is not possible to optimally benefit from all the advantages specific to xylitol.

By agglomerating crystallized xylitol powder having a very fine particle size using a sorbitol syrup with vigorous stirring, Patent EP 329 977 provides a binding and diluting agent, which can be used in direct compression, the granules of which have a size between 0.1 and 1 mm and contain 94 to 98 wt % of xylitol, 1 to 5 wt % or sorbitol, 0 to 2 wt % of other polyols, and less than 1 wt % of water.

This binding and diluting agent has a bulk density of the tapped product of 0.7 to 0.8 g/ml.

Prior milling of the xylitol to obtain a fine particle size, agglomeration using a sorbitol syrup having a low solids content, and also the final drying step of the powder do not give the method all the desired simplicity and constitute additional operations which increase its implementation cost.

Therefore, one particular objective of the present invention is to provide a method for manufacturing a powder containing crystalline particles of xylitol with another polyol which are less sensitive to the aforementioned disadvantages and which makes it possible to efficiently obtain a powder containing crystalline particles of xylitol having desirable properties.

According to the present invention, a method is provided for manufacturing crystalline particles of xylitol with another polyol which does not require a very high concentration of xylitol or any effort undertaken to accurately measure or control the temperature during the granulating/crystallizing step.

Furthermore, the method of the invention does not involve formation of massecuite, nor the application of a shear or kneading force, relying instead simply on a concurrent coating, agglomeration and induction of the crystallization while allowing the agglomerated mixture of xylitol with another polyol to mature at a temperature below the melting point of xylitol, to form solid granules.

According to the present invention, a method is provided for manufacturing a powder containing crystalline particles of xylitol and of another polyol, this process comprising the continuous mixing of a syrup of xylitol and of another polyol, having a solids content of at least 95 wt % and having a xylitol content of 85 to 97.5 wt % and a content of the other polyol of at least 15 to 2.5 wt % based on the solids content, the mixing being carried out by simultaneously dispersing the syrup of xylitol and of the other polyol with seeds containing xylitol in an open rotary container that contains xylitol-based granules, with which the syrup of xylitol and of the other polyol and the seeds containing xylitol are mixed at the surface of the xylitol-based granules contained in the container, the recovery of the granules based on xylitol and on the other polyol from the container, and the crystallization of the xylitol and of the other polyol contained in said granules, the granules based on xylitol in the container being kept moving by the rotation of the container.

During the implementation of the method of the invention, the syrup of xylitol and of the other polyol is preferably introduced into the container in a subdivided form, for example in the form of drops or globules, jets or groups of jets.

According to one preferred embodiment of the aforementioned method, a syrup of xylitol and of the other polyol, having a solids content of at least 95 wt %, is brought to a temperature of at least 80° C. and is continually mixed in a container with seeds containing xylitol, the seeds/syrup ratio, the dimensions, the orientation of the axis of rotation and the speed of rotation of the container being chosen such that the product recovered from the container appears in the form of granules having a diameter of around 100 to 10 000 μm.

The method of the invention may be carried out in a device comprising an open rotary container, with an axis of rotation which may be inclined horizontally, a means of supplying, to an area located inside the container, above the mass which partially fills it, and of dispersing therein one part of the syrup of xylitol and of the other polyol, preferably subdivided in the aforementioned forms, and some seeds containing xylitol, and a means of ensuring the mixing of the syrup of xylitol and of the other polyol and seeds containing xylitol, at the surface of the moving mass partially filling the container.

The xylitol-based granules are preferably recovered by overflowing at the outlet of the container and may be matured to increase their crystallinity, by transferring the granules into a rotating cylinder having dimensions such that the residence time of the granules originating from the container is sufficient to ensure the crystallization of xylitol and of the other polyol. The granules may then be transferred into a dryer to reduce the residual moisture content, and then into a means for milling and screening.

According to a first preferred embodiment of the method of the invention, it is possible to procure a xylitol and sorbitol syrup, of the type of that available commercially or it is possible to prepare it extemporaneously, so that its solids content is at least 95%, and so that its xylitol content is around 95% based on the solids content and its sorbitol content is around 5% based on the solids content and said syrup is dispersed at a temperature of around 80° C. inside an open rotary container in the form of an open drum or tank having a mainly flat bottom, of which the axis of rotation may be inclined in a horizontal plane having an angle of 25 to 450.

According to a second preferred embodiment of the method of the invention, it is possible to extemporaneously prepare a xylitol and sorbitol syrup of which the solids content is at least 95% and that has a xylitol content of around 85% based on the solids content and a sorbitol content of around 15% based on the solids content, said syrup is then dispersed at a temperature of around 80° C. inside an open rotary container in the form of an open drum or tank having a mainly flat bottom, of which the axis of rotation may be inclined in a horizontal plane having an angle of 25 to 45°.

According to a third preferred embodiment of the method of the invention, a xylitol and maltitol syrup is prepared extemporaneously of which the solids content is at least 95%, and that has a xylitol content of around 90% based on the solids content and a maltitol content of around 10% based on the solids content, and said syrup is dispersed at a temperature of around 80° C. inside an open rotary container in the form of an open drum or tank having a mainly flat bottom, of which the axis of rotation may be inclined in a horizontal plane having an angle of 25 to 45°.

An air atomizing nozzle is advantageously used, in these three preferred embodiments, to spray said aqueous syrup on the rotating bed of xylitol-containing seed materials, in a pilot-scale granulator.

The weight ratio in the mixture consisting of xylitol-containing seeds and xylitol and sorbitol (or maltitol) syrup is 1/1.

The mixing is carried out at the surface of the moving mass partially filling the container; the movement in question resembles a mass of pills inside a pill-making machine, and it is observed that granules which are increasingly large are formed, the largest granules having a tendency to come to the surface of the moving mass.

The granules of xylitol and of the other polyol thus obtained are then matured to increase their crystallinity.

This maturing step may be carried out by keeping the granules moving at a temperature below the melting point of the granules, preferably at a temperature of 5 to 85° C., for 1 to 20 hours, in a current of air.

The granulated product is then dried in order to obtain a residual moisture content that is not greater than around 1%.

The granules may then be milled to the required particle size and then sorted by screening; the particles removed by screening may advantageously be recycled to the aforementioned container, for use as seeds containing xylitol and the other polyol.

One very advantageous property of the powder containing crystalline particles of xylitol and of the other polyol according to the invention is that it has a compressive value, according to the test B, which is greater than 80 N, preferably greater than 100 N, more preferably still greater than 150 N, as will be exemplified below.

The test B consists in measuring the hardness, expressed in Newtons, of a tablet sample produced on a Carver press by a load of 18 kNewtons applied to a Carver No. 3619 13 mm pellet die, to obtain a tablet containing 0.9 g of powder containing crystalline particles of xylitol and of the other polyol (particle size cut: 250-425 μm) according to the invention and 1% of magnesium stearate.

The hardness of the tablet is determined in a Dr Schleuniger Pharmatron model 6D tablet tester.

The results show that the powder according to the invention, containing crystalline particles of xylitol and of the other polyol, has a high hardness value which, to the knowledge of the Applicant Company, has not yet been described.

The resulting powders containing crystalline particles of xylitol and of the other polyol are also characterized by the fact that they have a rate of solubilization in water, according to the test A, of less than 1 min, preferably between 20 and 30 seconds±5 seconds.

In order to measure this characteristic of the powder containing crystalline particles of xylitol and of another polymer according to the invention, namely the solubilization time, the test A is carried out.

The first step of the test A consists in carrying out the degassing of the water at 20° C., water which is placed with a magnetic stirrer bar (length 6.06 cm and diameter 1.15 cm) in a 2000 ml vacuum flask placed on a magnetic stirrer plate. The rotational speed of the bar (200 rpm) is adapted to create sufficient stirring. The vacuum is applied until the disappearance of bubbles, synonymous with the residual presence of dissolved gas.

The second step consists in screening the powder to be tested, so as to recover the fraction having a particle size between 315 and 500 μm.

Next, 150 g of degassed water is introduced into a 250 ml low-form transparent glass beaker (outer diameter 70 mm, height 96 mm) containing a cylindrical magnetic stirrer bar (length: 45 mm and diameter: 9.5 mm).

Said beaker, as prepared, is placed on a laboratory magnetic stirrer plate set at a rotational speed of 200 rpm.

Next, exactly and in a single go, 5 g of the screened powder is introduced and the timer is started.

When the solubilization is complete (no visibly detectable particles) the timer is stopped and, the time elapsed is noted.

Under these conditions, the powder containing crystalline particles of xylitol and of the other polyol according to the invention generally has a solubilization rate of less than a minute, preferably between 20 and 30 seconds±5 seconds.

In order to measure the bulk density of the powder containing crystalline particles of xylitol and of another polyol according to the invention, the test C is carried out.

The test C is intended to determine, under set conditions, the bulk volumes before and after tapping, the aptitude for tapping, and also the bulk densities of the powders obtained.

For the requirements of the test C, the powder containing crystalline particles of xylitol and of another polyol according to the invention is milled and screened so that a powder having a particle size between 100 and 1000 µm is obtained.

The apparatus is a STAV 2003 tapped volumeter sold by J. Engelsmann AG which is composed of:
- a tapping machine which may produce, per minute, 250 drops±15 drops from a height of 3 mm±0.2 mm. The test specimen support, with its attachment device, must have a mass of 450 g±5 g;
- a 250 ml test specimen that is graduated every 2 ml, whose mass must be 220 g±40 g.

Introduced without tapping into the dry test specimen is a test sample M of 100 g weighed with an accuracy of 0.5%. The test specimen is attached to its support. The bulk volume before tapping $V_0$, assessed to within 1 ml, is read.

It is subjected to 10, 500 and 1250 drops and the corresponding volumes $V_{10}$, $V_{500}$ and $V_{1250}$, assessed to within 1 ml, are read.

The bulk densities are given by the following expressions:
bulk density before tapping (known as the density of the loose product)=100/bulk volume before tapping; and
bulk density after tapping (known as the density of the tapped product)=100/bulk volume after 1250 drops.

The results show that the powder containing crystalline particles of xylitol and of the other polyol according to the invention has a tapped bulk density between 0.5 and 2 g/ml, preferably between 0.6 and 1 g/ml.

The present application also relates to the use of a powder according to the invention or which may be obtained by a method according to the invention, for manufacturing tablets.

The following examples illustrate the preparation of the powder containing crystalline particles of xylitol and of the other polyol by the use of the method according to the invention.

EXAMPLE 1

A solution having a xylitol content of 95% and a sorbitol content of 5%, based on the solids content, was placed in an evaporation container in order to obtain a xylitol and sorbitol syrup having a solids content of 95%.

This xylitol and sorbitol syrup was placed in a storage tank at a temperature of around 80° C., from which it was continually removed by means of a pump which ensured its dispersion in the form of globules by means of a nozzle.

At the same time as the dispersion of said xylitol and sorbitol syrup, additional seed material was continually introduced into the pilot-scale granulator to produce a seed/syrup weight ratio of around 1 part of seeds per 1 part of xylitol and sorbitol syrup.

The seeds were obtained by the continuous recycling of one fraction of the solidified material being produced.

Any crystalline xylitol solid particles could be used to provide seeds for the initial granulation.

No particular effort was undertaken to control the temperature of the granulator.

The granulator rotated at a speed of around 6.5 rpm, its inclination being 30°, which made it possible to obtain granules having an average diameter of around 500 µm to 10 000 µm.

After this granulating step, said granules were matured at 60° C. by completion of the crystallization in a maturing device (elongated rotary drum).

The matured granules thus obtained had a 97.3/2.7 composition of xylitol/sorbitol and were dried in a fluidized bed using air at around 45° C., then subjected to coarse milling.

The granules thus treated appeared in the form of a powder containing around 0.27% of residual moisture content.

The dried powder was then screened and formed the powder containing crystalline particles of xylitol and of sorbitol according to the invention.

The solubilization rate, as measured according to test A, was 30 seconds, and the hardness value determined according to test B was 130 N.

Table I below presents the results of the measurements carried out according to test C.

TABLE I

| 100 g of powder used 100-1000 µm fraction | |
| --- | --- |
| Bulk density before tapping (g/ml) | 0.588 |
| Average $V_0$ (ml) over 3 measurements | 170 |
| Average $V_{10}$ (ml) over 3 measurements | 162 |
| Average $V_{500}$ (ml) over 3 measurements | 150 |
| Average $V_{1250}$ (ml) over 3 measurements | 148 |

The bulk density of the loose product was thus 0.588 g/ml and the bulk density of the tapped product was 0.676 g/ml.

EXAMPLE 2

A solution having a xylitol content of 85% and a sorbitol content of 15%, based on the solids content, was placed in an evaporation container in order to obtain a xylitol and sorbitol syrup having a solids content of 95%.

This xylitol and sorbitol syrup was placed in a storage tank at a temperature of around 80° C., from which it was continually removed by means of a pump which ensured its dispersion in the form of globules by means of a nozzle.

At the same time as the dispersion of said xylitol and sorbitol syrup, additional seed material was continually introduced into the pilot-scale granulator to produce a seed/syrup weight ratio of around 1 part of seeds per 1 part of xylitol and sorbitol syrup.

The seeds were obtained by the continuous recycling of one fraction of the solidified material being produced.

Any crystalline xylitol solid particles could be used to provide seeds for the initial granulation.

No particular effort was undertaken to control the temperature of the granulator.

The granulator rotated at a speed of around 6.5 rpm, its inclination being 300, which made it possible to obtain granules having an average diameter of around 500 µm to 10 000 µm.

After this granulating step, said granules were matured in an oven at 60° C. for 30 to 40 minutes.

The matured granules thus obtained had a 90/10 composition of xylitol/sorbitol and were dried in a fluidized bed using air at around 45° C., then subjected to coarse milling.

The granules thus treated appeared in the form of a powder containing around 0.41% of residual moisture content.

The dried powder was then screened and formed the powder containing crystalline particles of xylitol and of sorbitol according to the invention.

The solubilization rate, as measured according to test A, was 20 seconds, and the hardness value determined according to test B was 170 N.

Table II below presents the results of the measurements carried out according to test C.

TABLE II

| 100 g of powder used 100-1000 μm fraction | |
|---|---|
| Bulk density before tapping (g/ml) | 0.645 |
| Average $V_0$ (ml) over 3 measurements | 155 |
| Average $V_{10}$ (ml) over 3 measurements | 150 |
| Average $V_{500}$ (ml) over 3 measurements | 137 |
| Average $V_{1250}$ (ml) over 3 measurements | 134 |

The bulk density of the loose product was thus 0.645 g/ml and the bulk density of the tapped product was 0.746 g/ml.

EXAMPLE 3

A solution having a xylitol content of 85% and a maltitol content of 15%, based on the solids content, was placed in an evaporation container in order to obtain a xylitol and maltitol syrup having a solids content of 95%.

This xylitol and maltitol syrup was placed in a storage tank at a temperature of around 80° C., from which it was continually removed by means of a pump which ensured its dispersion in the form of globules by means of a nozzle.

At the same time as the dispersion of said xylitol and maltitol syrup, additional seed material was continually introduced into the pilot-scale granulator to produce a seed/syrup weight ratio of around 1 part of seeds per 1 part of xylitol and maltitol syrup.

The seeds were obtained by the continuous recycling of one fraction of the solidified material being produced.

Any crystalline xylitol solid particles could be used to provide seeds for the initial granulation.

No particular effort was undertaken to control the temperature of the granulator.

The granulator rotated at a speed of around 6.5 rpm, its inclination being 30°, which made it possible to obtain granules having an average diameter of around 500 μm to 10 000 μm.

After this granulating step, said granules were matured in an oven at 70° C. for 30 to 40 minutes.

The matured granules thus obtained had a 90/10 composition of xylitol/maltitol and were dried in a fluidized bed using air at around 45° C., then subjected to coarse milling.

The granules thus treated appeared in the form of a powder containing around 0.37% of residual moisture content.

The dried powder was then screened and formed the powder containing crystalline particles of xylitol and of maltitol according to the invention.

The solubilization rate, as measured according to test A, was 23 seconds, and the hardness value determined according to test B was 95 N.

Table III below presents the results of the measurements carried out according to test C.

TABLE III

| 100 g of powder used 100-1000 μm fraction | |
|---|---|
| Bulk density before tapping (g/ml) | 0.794 |
| Average $V_0$ (ml) over 3 measurements | 126 |
| Average $V_{10}$ (ml) over 3 measurements | 118 |
| Average $V_{500}$ (ml) over 3 measurements | 108 |
| Average $V_{1250}$ (ml) over 3 measurements | 108 |

The bulk density of the loose product was thus 0.794 g/ml and the bulk density of the tapped product was 0.926 g/ml.

The invention claimed is:

1. A method for manufacturing a powder containing crystalline particles of xylitol and of at least one other polyol besides xylitol, comprising the steps of:
    a) providing xylitol-based granules;
    b) providing a syrup of xylitol and of at least one other polyol besides xylitol, said syrup having a solids content of at least 95 wt %, a xylitol content of 85 to 97.5 wt % based on the solids content and a content of said at least one other polyol of at least 15 to 2.5 wt % based on the solids content;
    c) providing seeds containing xylitol;
    d) continuously dispersing, in a rotating open rotary container, the seeds containing xylitol and the syrup of xylitol and of said at least one other polyol onto the xylitol-based granules, in a given seeds/syrup weight ratio, to obtain xylitol-based granules covered by a mixture of the seeds containing xylitol and of the syrup of xylitol and of the said at least one other polyol;
    e) recovering the xylitol-based granules of step d) from the rotating open rotary container; and
    f) crystallizing the xylitol and of said at least one other polyol of said xylitol-based granules of step e) to obtain the powder containing crystalline particles of xylitol and of said at least one other polyol.

2. The method as claimed in claim 1, wherein said at least one other polyol is selected from the group consisting of threitol, erythritol, arabitol, ribitol, sorbitol, mannitol, maltitol, maltotriitol, maltotetraitol, lactitol, hydrogenated isomaltulose, glycerol and hydrogenated starch hydrolysates, taken alone or in combination.

3. The method as claimed in claim 1, wherein said at least one other polyol is selected from the group consisting of sorbitol, maltitol, mannitol and hydrogenated isomaltulose, taken alone or in combination.

4. The method as claimed in claim 1, wherein the syrup of xylitol and of said at least one other polyol is introduced into the container in a subdivided form.

5. The method as claimed in claim 4, wherein the syrup of xylitol and of said at least one other polyol is introduced in drop form.

6. The method as claimed in claim 4, wherein the syrup of xylitol and of said at least one other polyol is introduced in the form of jets.

7. The method as claimed in claim 1, wherein the axis of rotation of the container is inclined relative to a horizontal plane.

8. The method as claimed in claim 1, wherein the granules based on xylitol and on said at least one other polyol are recovered by overflowing at the outlet of the container.

9. The method as claimed in claim 1, wherein granules having a diameter of 100 to 10,000 μm are recovered.

10. The method as claimed in claim 1, wherein a syrup of xylitol and of said at least one other polyol, having a solids content of 95 wt %, is brought to a temperature of at least 80°

C. and is continually mixed with seeds containing xylitol, the seeds/syrup weight ratio, the dimensions, the orientation of the axis of rotation and the speed of rotation of the container being selected such that the product recovered from the container appears in the form of granules having a diameter of 100 to 10,000 μm.

11. The method as claimed in claim 10, wherein the seeds/syrup weight ratio is about 1/1.

12. The method as claimed in claim 1, wherein the container is in the form of an open drum or tank having a mainly flat bottom.

13. The method as claimed in claim 12, wherein the axis of rotation of the container makes an angle of 25 to 45° relative to a horizontal plane.

14. The method as claimed in claim 1, wherein the granules of xylitol and of said at least one other polyol recovered are matured in order to increase their crystallinity by keeping the granules at a temperature of 5 to 90° C. for 1 to 20 hours while keeping the granules moving in a current of air.

* * * * *